United States Patent [19]

Christensen et al.

[11] Patent Number: 5,547,978
[45] Date of Patent: Aug. 20, 1996

[54] DERIVATIVES OF PYRROLIDIN-2-YLCARBONYLHETEROCYCLIC COMPOUNDS

[75] Inventors: Burton G. Christensen, Lebanon, N.J.; Takashi Egawa; Yasuyuki Ichimaru, both of Yokohama, Japan; Shokichi Ohuchi, Tokyo, Japan; Tsuneo Okonogi, Yokohama, Japan; Arthur A. Patchett, Westfield, N.J.; Seiji Shibahara, Tokyo; Seiji Tsutsumni, Yokohama, both of Japan

[73] Assignee: Meiji Seika Kaisha, Ltd., Tokyo, Japan

[21] Appl. No.: 346,240

[22] Filed: Nov. 23, 1994

Related U.S. Application Data

[63] Continuation-in-part of Ser. No. 6,105, Jan. 15, 1993, abandoned.

[51] Int. Cl.$^6$ ............... C07D 207/06; C07D 209/08; C07D 277/06; A61K 31/40
[52] U.S. Cl. ................ 514/422; 514/412; 514/365; 548/200; 548/468; 548/518
[58] Field of Search ............... 548/468, 519, 548/200; 514/422, 412, 365

[56] References Cited

U.S. PATENT DOCUMENTS

| | | | |
|---|---|---|---|
| 4,810,721 | 3/1989 | Saitoh | 514/422 |
| 4,826,870 | 5/1989 | Higuchi | 514/422 |
| 4,857,524 | 8/1989 | Furukawa | 514/227.5 |
| 4,873,342 | 10/1989 | Tanaka | 548/518 |
| 4,912,128 | 3/1990 | Henning | 514/422 |
| 4,916,146 | 4/1990 | Tanaka | 574/365 |
| 5,028,604 | 7/1991 | Torizuka | 514/227.8 |
| 5,118,811 | 6/1992 | Uchida | 548/200 |
| 5,198,458 | 3/1993 | Hiuchi | 514/397 |
| 5,407,950 | 4/1995 | Okubo | 514/365 |
| 5,449,787 | 9/1995 | Miyashita | 548/362.5 |
| 5,459,131 | 10/1995 | Albright | 514/19 |

OTHER PUBLICATIONS

Tsutsumi, Bioorganic & Medicinal Chemistry Letters, vol. 4, No. 6, pp. 831–834, 1994.
Szirtes, J. Med. Chem., vol. 27, pp. 741–745, 1984.
Chemical Abstracts, 115:280575, Kimura, 1991.
Chemical Abstracts, 115:280568, Kimura, 1991.
Chemical abstracts, 115:9341, Kohmura, 1991.
Chemical Abstracts, 114:247751, Tsunematsu, 1991.
Chemical Abstracts, 109:231501, Anteunis, 1988.
Chemical Abstracts, 108:222083, Van der Auwera, 1988.
Chemical Abstracts, 107:130409, Sakura, 1987.
Chemical Abstracts, 96:98505, Yoshida, 1982.

*Primary Examiner*—C. Warren Ivy
*Assistant Examiner*—D. Margaret M. Mach
*Attorney, Agent, or Firm*—Varndell Legal Group

[57] ABSTRACT

The invention relates to derivatives of pyrrolidin-2-ylcarbonylheterocyclic compound of the general formula

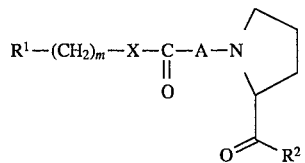

in which $R^1$ represents $C_{1-6}$ alkyl, $C_{1-20}$ cycloalkyl, aryl or heteroaryl, $R^2$ represents a heterocyclic compound selected from the group consisting of 2-thiazole, 2-oxazole, 2-imidazole, 2-pyrrole, 2-thiophene, 2-benzothiazole, 2-benzoxazole, 2-benzimidazole, 2-indole, 2-thiazolo[5,4-b]pyridine, 2-oxazolo[4,5-b]pyridine, 2-imidazo[4,5-b]pyridine, 5-thiazole, 2-thiazoline, 2-pyridine, 3-pyridine, 5-pyrimidine, 2-pyrazine, 2-triazole or 2-pyrazole wherein the heterocyclic compound may be unsubstituted or substituted independently with $R^4$ or $R^5$ wherein $R^4$ and $R^5$ are H, $C_{1-5}$ alkyl, aryl or $R^4$ and $R^5$ may be ortho substituents on the heterocyclic compounds and connected to form an aryl or heteroaryl ring, A represents a cyclic amino acid, X is oxygen atom, thiomethlene or methylene residue, m is an integer from 1 to 5, to a process for the preparation thereof, to composition containing them, and to the use thereof.

13 Claims, No Drawings

DERIVATIVES OF PYRROLIDIN-2-YLCARBONYLHETEROCYCLIC COMPOUNDS

This application is a continuation-in-part of U.S. Ser. No. 08/006,105, filed Jan. 15, 1993 now abandoned

BACKGROUND OF THE INVENTION

This invention relates to pyrrolidin-2-ylcarbonylheterocyclic compounds and their physiologically acceptable salts which exhibit inhibitory activity on prolyl endopeptidase and are useful for the treatment of amnesia or Alzheimer's Disease. The compounds are also useful as cognitive enhancers and assist in memory retention.

It is hitherto known that prolyl endopeptidase (PEP) [EC 3.4.21.26] has the substrate specificity on peptide hormones which contain proline like substance P, thyrotropin releasing hormone, neurotensin and vasopressin, and inactivates them. Among the above peptides vasopressin is considered to be concerned with memory process (*Life Science*, vol. 19, p. 685 (1976) and *Science*, vol. 221, p. 601 (1981)). Yoshimoto et al. reported that inhibitors against PEP are effective on experimental amnesia in rats and PEP inhibitors are concerned with memory process (Seikagaku, vol. 55, p. 831 (1983), *Nippon Nogeikagaku Katshi*, vol. 58, p. 1147 (1984) and Japanese Patent Application Laid-open (Kokai) No. 172929/1985). From the above facts it seemed to be possible that PEP inhibitors are useful on the treatment and prevention of amnesia (*Journal of Pharmacobio-Dyn*, vol. 10, p. 730 (1987)).

On the other hand some pyrrolidine analogs which have 2-chloromethylcarbonyl, 2-diazomethylcarbonyl or 2-formyl residue on their carboxyl terminal ends are reported to have PEP-inhibitory activity (*Biochemistry*, vol. 16, p. 2942 (1977) and *Journal of Neurochemistry*, vol. 41, p. 69 (1983)). Furthermore, related amino acid analogs which have a—$COCO_2R$, —$COCONR'R''$, —$COCF_3$, —$COCF_2CO_2R$ or —$COCF_2NR'R''$ residue on the carboxyl terminal end are reported but there are no descriptions on PEP inhibiting activity (European Patent Application No. 320753/1989).

SUMMARY OF THE INVENTION

The object of this invention is to provide novel pyrrolidin-2-ylcarbonylheterocyclic compounds possessing an excellent activity on prolyl endopeptidase. The other object of this invention is to provide a pharmaceutical use of such pyrrolidin-2-ylcarbonylheterocyclic compounds. Compounds claimed in the instant invention and the claimed pharmaceutical compositions are useful as a method of treating amnesia in mammals, including humans, wherein a pharmaceutically effective amount of the claimed composition is administered to a mammalian organism in need of treatment thereof. The claimed compounds and compositions can also be used to treat Alzheimer's Disease and other cognitive disorders wherein a pharmaceutically effective amount of the claimed composition is administered to a patient in need of treatment thereof. The claimed compositions are also useful as a method of enhancing cognition and memory retention in mammalian organisms. The instant invention also claims a method of inhibiting PEP in a mammalian brain comprising administering an oral or other suitable dosage of a pharmaceutically effective amount of the claimed compounds or compositions.

DETAILED DESCRIPTION

This invention relates to a novel pyrrolidin-2-llycarbonylheterocyclic compounds of the general formula (I)

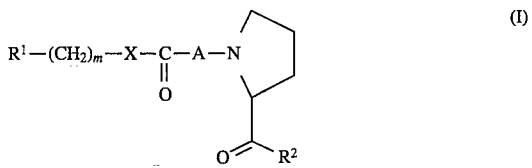

wherein $R^1$ is optionally branched lower alkyl having less than 6 carbon atoms, aryl having a mono- or polycyclic system composed of 5- and/or 6 membered aromatic rings either unsubstituted or substituted with $R^6$ (wherein $R^6$ is halogen, nitro, methyl or methoxy group), cycloalkyl having less than 20 carbon atoms or heteroaryl having a mono- or polycyclic system composed of 5- and/or 6 membered aromatic rings containing 1, 2 or 3 heteroatoms chosen from N, O or S either unsubstituted or substituted with $R^7$ (wherein $R^7$ is halogen, nitro, cyano, methyl, hydroxy, methoxy or amino group). $R^1$ as aryl can be, for example, pheyl, naphthyl, indanyl or tetrahydronaphthyl group, $R^1$ as heteroaryl can be, for example, thienyl, furyl, pyrrolydinyl, pyridinyl, pyrimidinyl, pyrazinyl, pyridazinyl, 2,3-benzofuranyl, benzothienyl, indolyl or indolinyl group. $R^2$ is optionally a substituted heterocyclic compound selected from the group consisting of 2-thiazole, 2-oxazole, 2-imidazole, 2-pyrrole, 2-thiophen, 2-(3,4-dimethylthiazole), 2-benzothiazole, 2-benzoxazole, 2-benzimidazole, 2-indole, 2-thiazolo[5,4b]pyridine, 2-oxazolo[4,5-b]pyridine, 2-imidazo[4,5-b]pyridine, 2-pyrrole, 5-thiazole, 2-thiazoline, 2-pyridine, 3-pyridine, 5-pyrimidine, 2-pyrazine, 2-triazole or 2-pyrazole; X is oxygen atom, thiomethylene residue or methylene residue; m is an integer of 1 to 5; A means a group selected from the group of the formula:

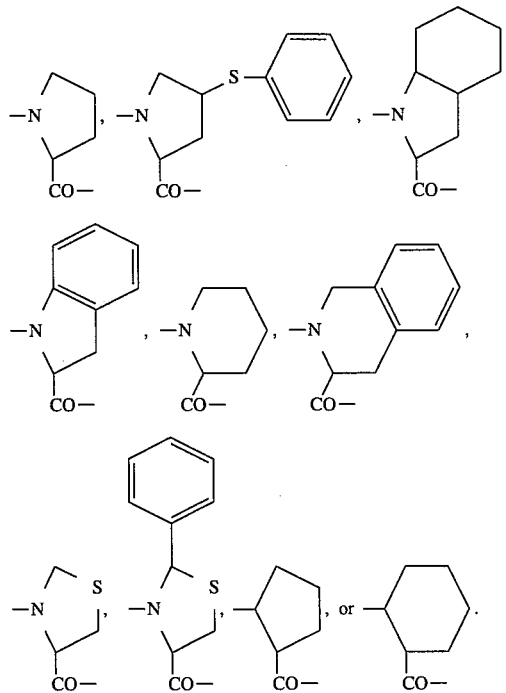

The invented compounds shown by the formula (I) have asymmetric carbon atoms so that there exist stereoisomers on each asymmetric carbon atom ((R) or (S) configuration). Those stereoisomers are also included in this invention.

The preferable compounds of this invention relate to the general formula (I) wherein $R^1$ is aryl or heteroaryl; $R^2$ is heterocyclic compound selected from the group consisting of 2-thiazole, 2-oxazole, 2-benzothiazole or 2-(4,5-dimethyl-thiazole); X is oxygen atom or methylene residue; m is an integer from 1 to 2; and A is a group selected from the group of the formula:

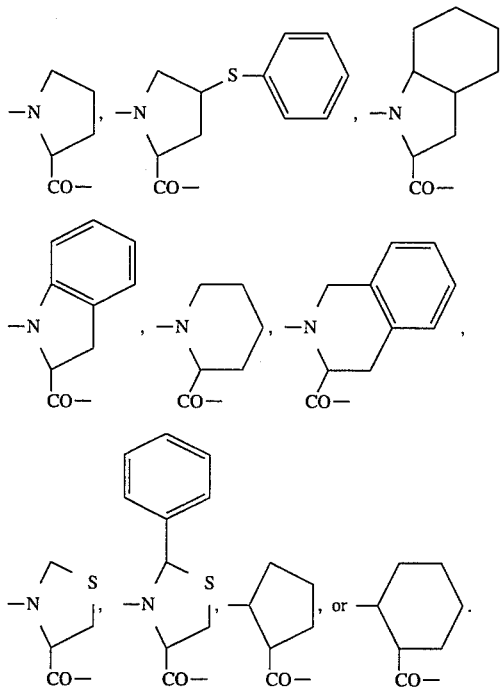

The preferable compounds of this invention include, for example, 2-[1-{1-(4-phenylbutanoyl)pyrrolidin-2(S)-ylcarbonyl}pyrrolidin-2(S)-ylcarbonyl]benzothiazole, 2-[1-{1-benzyloxycarbonyl -4(R)-phenylthiopyrrolidin 2(S)-ylcarbonyl}pyrrolidin-2(S)-ylcarbonyl]thiazole, 4-[1-(1-benzyloxycarbonylindolin -2(S)-ylcarbonyl)pyrrolidin-2(S)-ylcarbonyl}oxazole, 2-{1-(1-benzyloxycarbonylpyrrolidin-2(S)-ylcarbonyl)pyrrolidin-2(S)-ylcarbonyl}thiazole, 2-[1-(1-(4-phenylbutanoyl)pyrrolidin- 2(S)-ylcarbonyl}pyrrolidin-2(S)-ylcarbonyl]thiazole, 2-{1-( 1-benzyloxycarbonyloctahydroindol -2(S)-ylcarbonyl)pyrrolidin-2(S)-ylcarbonyl}thiazole, 2-[1-{1-(4-phenylbutanoyl)octahydroindol-2(S)-ylcarbonyl}pyrrolidin-2(S)-ylcarbonyl]thiazole, 2-{1-(1-benzyloxycarbonyl)indolin- 2(S)-ylcarbonyl)pyrrolidin-2(S)-ylcarbonyl}thiazole, 2-[1-{1-(4-phenylbutanoyl) indolin-2(S)-ylcarbonyl)pyrrolidin-2(S)-ylcarbonyl]thiazole, 2-[1-{1-(4-phenylbutanoyl)-4(R)-phenylthio-pyrrolidin -2(S)-ylcarbonyl}pyrrolidin-2(S)-ylcarbonyl]thiazole, 2-[1-{1(4-phenylbutanoyl)piperidin- 2(S)-ylcarbonyl}pyrrolidin-2(S)-ylcarbonyl]thiazole, 2-[1-{2-(4-phenylbutanoyl)-1,2,3,4-tetrahydro-isoquinolin -3-ylcarbonyl}pyrrolidin-2(S)-ylcarbonyl]thiazole, 2-[1-{3-(4-phenylbutanoyl)thiazolin-4(R)-ylcarbonyl}pyrrolidin-2(S)-ylcarbonyl]thiazole, 2-[1-(2-benzylthioacetylcyclopentan-1-ylcarbonyl)pyrrolidin-2 (S)-ylcarbonyl]thiazole, 2-[1-(2-benzylthioacetylcyclohexan-1-ylcarbonyl) pyrrolidine-2(S)-ylcarbonyl]thiazole, 2-[1-{3-(4-phenylbutanoyl)- 2(S)-phenylthiazolin-4(R)-ylcarbonyl}pyrrolidin-2(S)-ylcarbonyl]thiazole, 2-{1-(1-benzyloxycarbonylpyrrolidin-2(S)-ylcarbonyl)pyrrolidin-2(S)-ylcarbonyl}benzothiazole, 2-{1-(1-benzyloxycarbonylindolin -2(S)-ylcarbonyl)pyrrolidin-2(S)-ylcarbonyl}benzothiazole, 2-[1-{1-(4-phenylbutanoyl)indolin-2(S)-ylcarbonyl}pyrrolidin-2(S)-ylcarbonyl] benzothiazole, 2-{1-(1-benzyloxycarbonyl -4(R)-phenylthiopyrrolidin-2(S)-ylcarbonyl)pyrrolidin- 2(S)-ylcarbonyl}benzothiazole, 4-[1-{1-(4-phenylbutanoyl)-4(R) -phenylthiopyrrolidin-2(S)-ylcarbonyl}pyrrolidin-2(S)-ylcarbonyl]benzothiazole, 2-[1-(2-benzylthioacetylcyclohexan-1-ylcarbonyl)pyrrolidin- 2(S)-ylcarbonyl]benzothiazole, 4-[1-{1-(4-phenylbutanoyl)pyrrolidin- 2(S)-ylcarbonyl}pyrrolidin-2(S)-ylcarbonyl]oxazole, 4-[1-{1-(4-phenylbutanoyl)indolin-2(S)-ylcarbonyl}pyrrolidin-2(S)-ylcarbonyl]oxazole, 2-{1-(1-benzyloxycarbonylpyrrolidin -2(S)-ylcarbonyl)pyrrolidin-2(S)-ylcarbonyl}thiophene, 2-[1-{1-(4-phenylbutanoyl)pyrrolidin-2(S)-ylcarbonyl}pyrrolidin-2(S)-ylcarbonyl]thiophene, 4,5-dimethyl-2-[1-{1(4-phenylbutanoyl)pyrrolidin- 2(S)-ylcarbonyl}pyrrolidin-2(S)-ylcarbonyl]thiazole, 2-[1-{1-(4-phenylbutanoyl)pyrrolidin-2(S)-ylcarbonyl}pyrrolidin-2(S)-ylcarbonyl]-1H-imidazole, 2-[1-{1-(4-phenylbutanoyl)pyrrolidin -2(S)-ylcarbonyl}pyrrolidin-2(S)-ylcarbonyl]-1H-benzimidazole, 3-[1-{1-(4-phenylbutanoyl)pyrrolidin-2(S)-ylcarbonyl}pyrrolidin-2(S)-ylcarbonyl]pyridine, 5-[1-{1-(4-phenylbutanoyl)pyrrolidin- 2(S)-ylcarbonyl}pyrrolidin-2(S)-ylcarbonyl]pyrimidine, 2-[1-{1-(4-phenylbutanoyl) pyrrolidin-2(S)-ylcarbonyl}pyrrolidin-2(S)-ylcarbonyl]pyridine, 5-[1-{1-(4-phenylbutanoyl)pyrrolidin- 2(S)-ylcarbonyl}pyrrolidin-2(S)-ylcarbonyl]thiazole, 3-[1-{1-(4-phenylbutanoyl)pyrrolidin-2(S)-ylcarbonyl}pyrrolidin-2(S)-ylcarbonyl]-1,2,4-triazole, 2-[1-{1-(4-phenylbutanoyl)pyrrolidin- 2(S)-ylcarbonyl}pyrrolidin-2(S)-ylcarbonyl]pyrazole, 2-[1-{1-(4-phenylbutanoyl)pyrrolidin-2(S)-ylcarbonyl}pyrrolidin-2(S)-ylcarbonyl]benzoxazole, 2-[1-{1-(4-phenylbutanoyl)pyrrolidin- 2(S)-ylcarbonyl}pyrrolidin-2(S)-yl]oxazolo[4,5-b]pyridine, 2-[1-{1-(4-phenylbutanoyl)pyrrolidin-2(S)-ylcarbonyl}pyrrolidin-2(S)-ylcarbonyl]imidazo[4,5-b]pyridine, 2-{1-(1-benzyloxycarbonyl)pyrrolidin-2(S)-ylcarbonyl)pyrrolidin-2(S)-ylcarbonyl}benzimidazole, 2-methoxy-3-[1-{1-(4-phenylbutanoyl)pyrrolidin- 2(S)-ylcarbonyl}pyrrolidin-2(S)-ylcarbonyl]pyrazine, 2-[1-{1-(4-phenylbutanoyl)pyrrolidin-2(S)-ylcarbonyl}pyrrolidin-2(S)-ylcarbonyl]thiazoline or their pharmaceutically acceptable salts or hydrates.

The pyrrolidine-2-ylcarbonylheterocyclic compounds of the present invention can be produced by the following methods. Method A comprises reacting a suitable prolinal derivative with a compound of the formula:

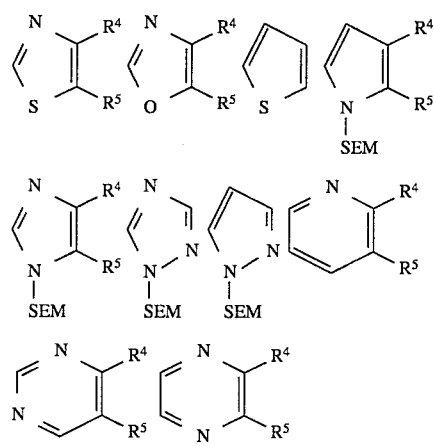

wherein $R^4$ and $R^5$ are the same or different and respectively mean hydrogen or halogen, optionally branched lower alkyl or alkoxy having less than 5 carbons atoms or optionally substituted phenyl (wherein the phenyl is optionally substituted with halogen, nitro, cyano, carboxyl, carbomethoxy, methyl, hydroxy, methoxy or amino group), $R^4$ and $R^5$ can be combined to give a cyclic compound with methylene residue, —CH═CH—CH═CH— residue or —CH═CH—CH═N— residue, and SEM means trimethylsillylethoxymethyl group. The above aromatic heterocycle(s) is reacted with N-protected prolinal to give a compound of the general formula (II):

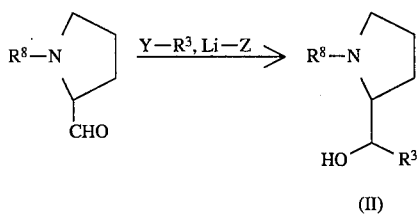

Wherein $R^8$ is tert-butoxycarbonyl (Boc) or allyloxycarbonyl (Alloc), Y is a proton or halogen, Z is n-butyl, diisopropylamine or tetramethyl-piperidine and $R^3$ means a group selected from heterocyclic compounds shown below:

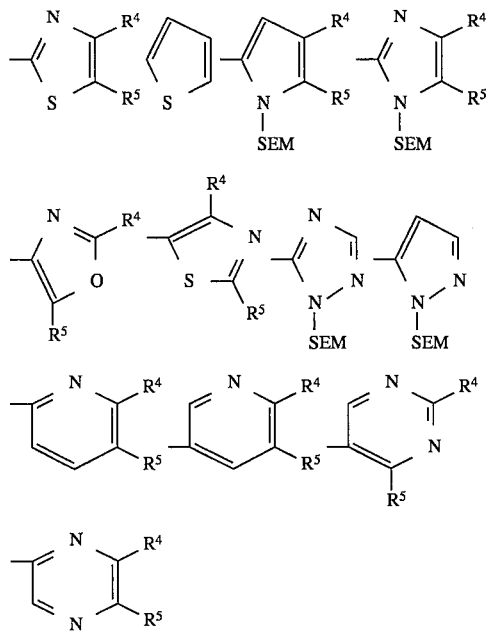

wherein $R^4$ and $R^5$ are as defined above.

This reaction is conducted in an inert organic solvent like tetrahydrofuran (THF), 1,2-dimethoxyethane and the like in presence of a base (n-butyllithium, tert-butyllithium, sodium hydride or the like) at −75° C. to 0° C.

Method B comprises treatment of cyanohydrine with anhydrous HCl and ethanol followed by cyclization with aminoalcohol derivatives or aminothiol derivatives to give a compound the general formula (II).

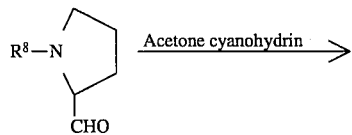

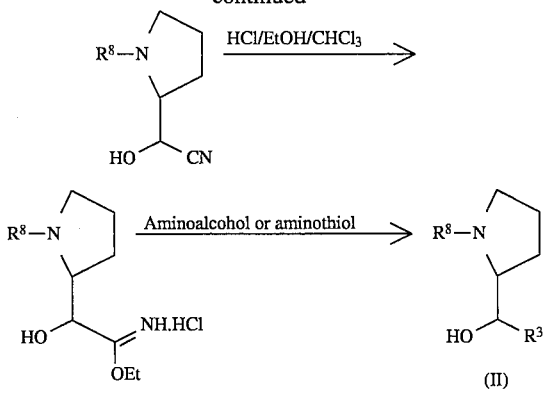

Whereto $R^8$ is defined above, and $R^3$ means a group selected from heterocyclic compounds show below:

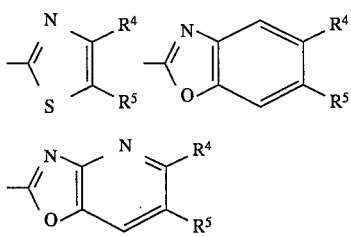

wherein $R^4$ and $R^5$ are as defined above.

The reaction product of the compound having general formula (II) is subjected to a deprotection reaction to afford a compound of the general formula (III):

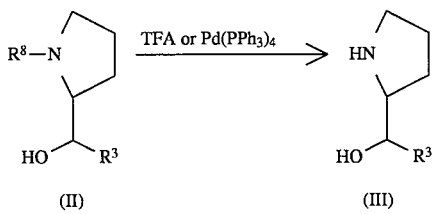

wherein $R^3$ is as defined above.

The deprotection is a standard method in peptide chemistry by an organic or inorganic acid like trifluoroacetic acid, hydrogen bromide, hydrogen chloride or tetrakis(triphenylphosine)palladium(Pd(PPh$_3$)$_4$) and the like.

The produced compound (III) is reacted with an acid compound of the general formula (IV) to give an acyl compound of the general formula (V).

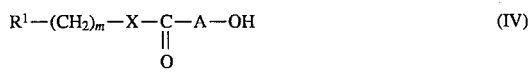

wherein $R^1$, $R^3$, X, A and m are as defined above.

The reaction scheme for converting the compound (III) to the acyl compound of the general formula (V) can be as follows:

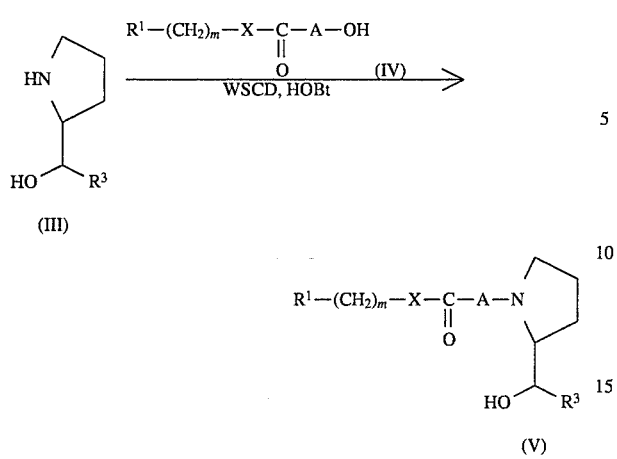

(III)

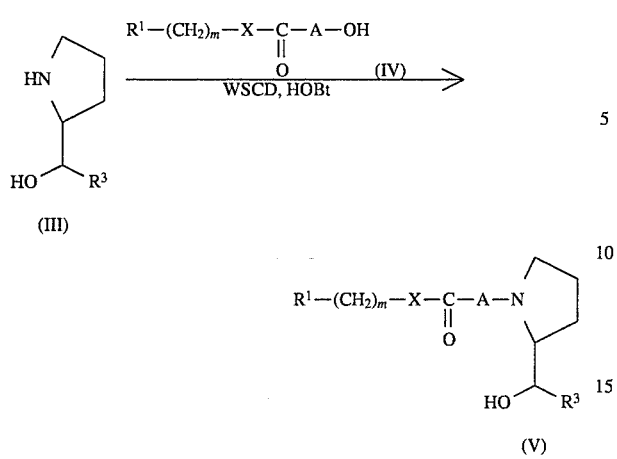

(V)

wherein $R^1$, $R^3$, X, A and m are as defined above. The acylation reaction is conducted by a standard method in peptide chemistry such as an acid chloride reaction, acid anhydride reaction, activate ester reaction and the like or in the presence of a coupling reagent such as water soluble carbodiimide (WSCD) or dicyclohexylcarbodiimide (DCC).

The acylated compound of the general formula (V) but without the SEM protecting group can be subjected to an oxidation reaction to give the compound of general formula (I). The oxidation reaction is performed with dimethylsulfoxide (DMSO) in the presence of oxalyl chloride, DCC or trifluoroacetic anhydride. Sulfur trioxide pyridine complex is another reagent that can be used for the oxidation. The reaction is conducted in an appropriate organic solvent like methylene chloride, chloroform, DMSO and the like at $-50°$ C. to room temperature.

In the case where the acylated compound of the general formula (V) with an SEM protecting group was subjected to the oxidation reaction mentioned above to give a compound of the general formula (VI):

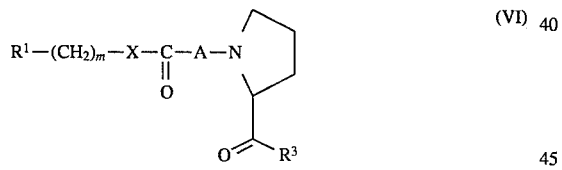

wherein $R^1$, $R^3$, X, A and m are as defined above, it can be followed by the deprotection reaction of SEM group to give the general formula (I).

The deprotection reaction of SEM group of the compound of the general formula (VI) is performed by tetrabutylammonium fluoride in THF under heating or by the reaction with hydrogen chloride in alcohol solution under heating.

A carboxylic acid compound of the general formula (IV) is produced by the following two methods.

1) In the case of a compound A which is derived from amino acid, a carboxylic compound of the general formula (VII):

wherein $R^1$, X and m have the same meaning defined above is converted to the acid chloride, an activated ester, or a mixed acid anhydride by the reaction with chloroformate and followed by the reaction with compound A to give a compound of the general formula (IV).

2) In the case of a compound A which is derived from a cyclicdicarboxylic acid like 1,2-cyclopentanedicarboxlic acid and 1,2-cyclohexanedicarboxlic acid, a dicarboxylic acid is converted to mono ester. The carboxyl group of the mono ester is converted to the acid chloride by the reaction with oxalyl chloride or thionyl chloride. The acid chloride is successively treated with diazomethane, hydrogen chloride and benzylmercaptane to give a benzylthiomethylcarbonyl compound. The produced benzylthiomethylcarbonyl compound is hydrolyzed by a standard method to give a compound of general formula (IV).

EXPERIMENTAL EXAMPLES

1) Prolyl Endopeptidase-Inhibitory Activity

The prolyl endopeptidase-Inhibitory activity was estimated in vitro with porcine kidney enzyme which was prepared according to methods of Walter and Yoshimoto et al. (*J. Biol. Chem*, vol. 251, p. 7593 (1976), *Biochem. Biophysic. Acta*, vol. 569, p. 184 (1979)).

A test compound (2 mg) was dissolved in DMSO (2 ml) and diluted to appropriate concentrations with DMSO. Z-Gly-Pro-p-nitroanilide (8 mg), a substrate was dissolved in dioxane (5 ml), water (27 ml) and 0.2 M phosphate buffer (pH 7.8, 40 ml). The substrate solution (180 ml) was mixed with an inhibitor solution (3 ml) and followed by addition of above mentioned porcine kidney enzyme solution (20 ml). Immediately after the mixing the UV absorbance at 405 nm was detected. The mixture was incubated at 37° C. for 20 min. and the UV absorbance was checked. A standard curve of absorbance (OD) vs. p-nitroaniline concentration was used to relate the absorbance to amount of substrate hydrolyzed. From two UV absorbance values $\Delta OD$ was determined to give the inhibiting activity of the compound. The inhibiting activity was obtained following the equation below. The $IC_{50}$ value was estimated from the inhibitor concentration vs. inhibitory activity curve.

The percent inhibitory activity $(\%) = (\Delta OD_c - \Delta OD_s)/\Delta OD_c \times 100$ $\Delta OD_s$: $\Delta OD$ for test sample $\Delta OD_c$: $\Delta OD$ for control The PEP inhibitory activities of compounds in this invention are shown in Table 1.

2) Ex vivo experiment

Ex vivo enzyme inhibition studies were performed to assess the degree of CNS availability and prolyl endpeptidase inhibition after oral administration. Compounds were dissolved in a minimal mount of ethanol (about 10% total volume) and made up to the appropriate volume with 1% polyoxyether sorbitan monooleate (Tween 80). Rats were dosed p.o. and at the appropriate times killed. The brains were removed, homogenised in the ice-cooled assay buffer, and centrifugated. Prolyl endopeptidase activities of the supernatant were assayed as described above, and the results are shown in Table 2. With respect to brain prolyl endopeptidase inhibition, the compound of Example 1 was more potent than SUAM-1221 and showed longer duration of action.

TABLE 2

| No. | Dose (mg/kg) | PEP Actively in brain (% of control) | | | | | |
|---|---|---|---|---|---|---|---|
| | | 0.25 | 0.5 | 1 | 2 | 4 | 6 (hr) |
| Compound of Example 1 | 10 | 42 | 21 | 32 | 47 | 69 | 98 |
| SUAM-1221* | 300 | 15 | 52 | 100 | 100 | 100 | 100 |

*N-[N-(4-phenylbutyryl)-L-prolyl]pyrrolidine

REFERENCE EXAMPLE

2-{1-(Pyrrolidin-2(S)-yl)hydoxymethyl}benzothiazole.

(a) 2-{1-(1-tert-Butoxycarbonylpyrolidin-2(S)-yl)hydoxymethyl}benzothiazole:

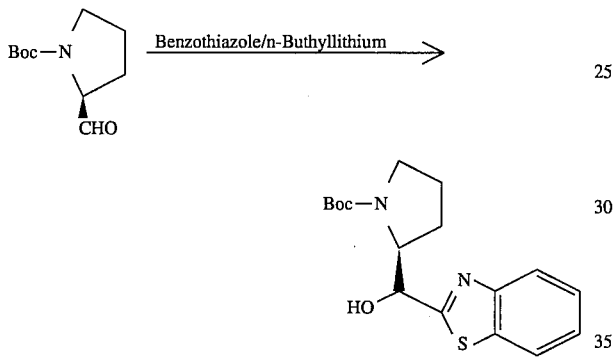

A 1.66M solution of n-buthlyllithium in hexane (2.30 ml, 4.0 mmol) was added dropwise to a solution of benzothiazole (540 mg, 4.0 mmol) in dry THF (10 ml) at −65° C. over 5 minutes. After 30 minutes a solution of Boc-(S)-(+)-2-pyrrolidinecarboxaldehyde (0.7 g, 5 mmol) in dry THF (5 ml) was added and the mixture was stirred at −65° C. for 4 hrs. Water (5 ml) was added at −65° C. and the mixture was poured into 1N hydrochloric acid and extracted with $CH_2Cl_2$. The combined extracts was evaporated, purified by column chromatography on silica gel to give a mixture of the two diastereomers as a yellow solid (1.02 g, 87.4%). FD-MS m/z 334 (M$^+$); NMR(CDCl$_3$) δ1.47–1.52(d, 9H), 1.94–1.98 (m, 1H), 2.05–2.25 (m, 1H), 2.35–2.45 (m, 1H), 2.82–2.85 (m, 1H), 3.26–3.47 (m, 2H), 4.15–4.50 (m, 1H), 4.97–5.22 (m, 1H), 6.61–6.88 (br.s, 1H), 7.35–7.39 (m, 1H), 7.44–7.52 (m, 1H), 7.89–7.91 (d, 1H), 7.97–7.99 (d, 1H).

(b)
2-{1-(Pyrrolidin-2(S)-yl)hydoxymethyl}benzothiazole:

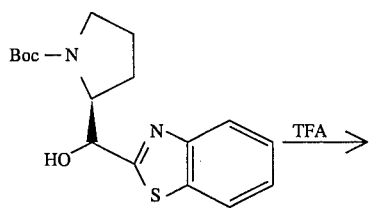

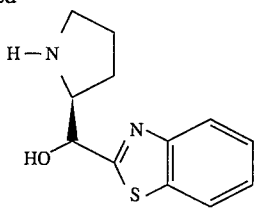

A solution of alcohol described above (2.45 g, 7.2 mmol) in 90% trifluoroacetic acid (TFA) (5 ml) was stirred at 0° C. for 30 minutes. The solution was concentrated and the resultant oil was dried. It was dissolved with saturated sodium bicarbonate and extracted with chloroform (6×100 ml). The organic phase was dried over MgSO$_4$ and concentrated to give the desired amine (1.30 g, 75.7%) as a red oil which was used without further purification. FD-MS m/z 234 (M$^+$); NMR(CDCl$_3$) δ1.75–2.00 (m, 4H), 3.78–3.81 (m, 2H), 4.75–4.76 (m, 1H), 5.04–5.08 (m, 1H), 7.35–7.39 (m, 1H), 7.44–7.48 (m, 1H), 7.89–7.91 (m, 1H), 7.95–7.98 (m, 1H).

EXAMPLE 1

2-[1-{1-(4-Phenylbutanoyl)pyrrolidin-2(S)-ylcarbonyl}pyrrolidin-2(S)-ylcarbonyl]benzothiazole.

(a) 2-[1-{1-(4-Phenylbutanoyl)pyrrolidin-2(S)-ylcarbonyl}pyrrolidin-2(S)-ylhydoxymethyl]benzothiazole:

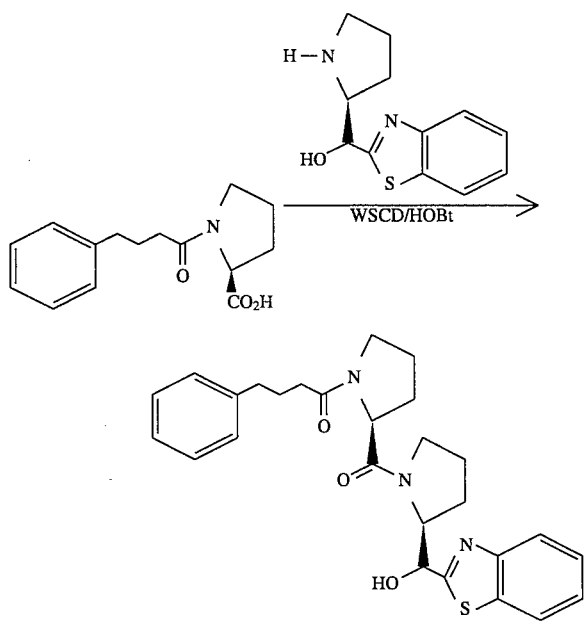

A solution of N-(4-phenylbutanoyl)-L-proline (130 mg, 0.4 mmol) and 2-{1-(pyrrolidin-2(S)-yl)hydroxymethyl}benzothiazole (94 mg, 0.4 mmol) in CH$_3$CN (10 ml) was cooled to 0° C. and treated with 1-hydroxybenzotriazole (HOB$_t$) (60.0 mg, 0.44 mmol) and water soluble carbodiimide (WSCD) (68.5 mg, 0.44 mmol). The solution was stirred overnight with gradual warming to room temperature. The solution was diluted with ethyl acetate, washed with saturated aqueous sodium bicarbonate, saturated aqueous sodium chloride, dried over MgSO$_4$, and concentrated. Purification of the residue by silica gel chromatography eluting with ethyl acetate provided the desired amide alcohol 170 mg (89%) as a mixture of two diastereomers. FD-MS m/z 447 (M⁺); NMR (CDCl₃) δ1.80–2.10 (m, 6H), 2.15–2.20 (m, 2H), 2.25–2.38 (m, 3H), 2.51–2.56 (m, 1H), 2.65–2.69 (m, 2H), 3.34–3.98 (m, 4H), 4.52–5.21 (m, 3H), 7.15–7.26 (m, 5H), 7.34–7.47 (m, 2H), 7.87–7.91 (m, 1H), 7.94–7.98 (m, 1H).

2-[1-{1-(4-Phenylbutanoyl)pyrrolidin-2(S)-ylcarbonyl}pyrrolidin-2(S)-ylcarbonyl]benzothiazole

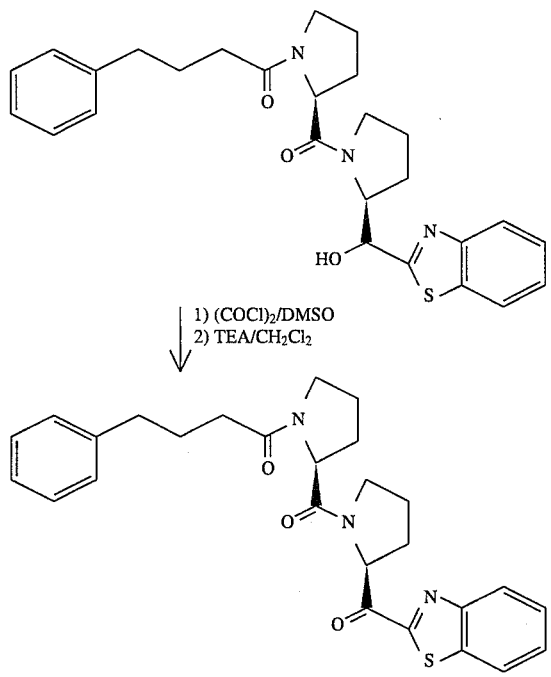

A solution of oxalyl chloride (27.41µl, 0.31 mmol) in CH₂Cl₂ (10 ml) at −60° C. was treated with DMSO (441µl, 0.63 mmol) and stirred for 10 minutes. Proline amide alcohol (100 mg, 0.21 mmol) was added and stirred at −60° C. for 1 hr. Triethylamine (143 mg, 1.42 mmol) was added and stirred for 0.5 h at −600° C. and the mixture allowed to warm to 0° C. over 0.5 hrs. The mixture was diluted with CH₂Cl₂, washed with water and brine, dried over MgSO₄ and evaporated. Purification of the residue by flash chromatography on silica gel (40 g) eluting with toluene/ethyl acetate (1:1) gave the desired heterocyclic ketone as a white foam (79.3 mg, 80%). FD-MS m/z 475 (M⁺); NMR (CDCl₃) δ1.86–2.25 (m, 9H), 2.15–2.25 (m, 2H), 2.37–2.43 (m, 1H), 2.56–2.60 (m, 2H), 3.31–3.33 (m, 1H), 3.45–349 (m, 1H), 3.64–3.70 (m, 1H), 3.94–3.98(m, 1H), 4.67–4.69 (m, 1H), 5.77–5.81 (m, 1H), 7.15–7.41 (m, 5H), 7.43–7.49 (m, 2H), 7.87–7.91 (m, 1H), 8.08–8.12 (m, 1H).

EXAMPLE 2

2-[1-{1-Benzyloxycarbonyl-4(R)-phenylthiopyrrolidin-2(S)-ylcarbonyl}-pyrrolidin-2(S)-ylcarbonyl]thiazole (a) 2-[1-{1-Benzyloxycarbonyl-4(R)-phenylthiopyrrolidin-2(S)-ylcarbonyl}pyrrolidin-2(S)-yl-hydoxymethyl]thiazole:

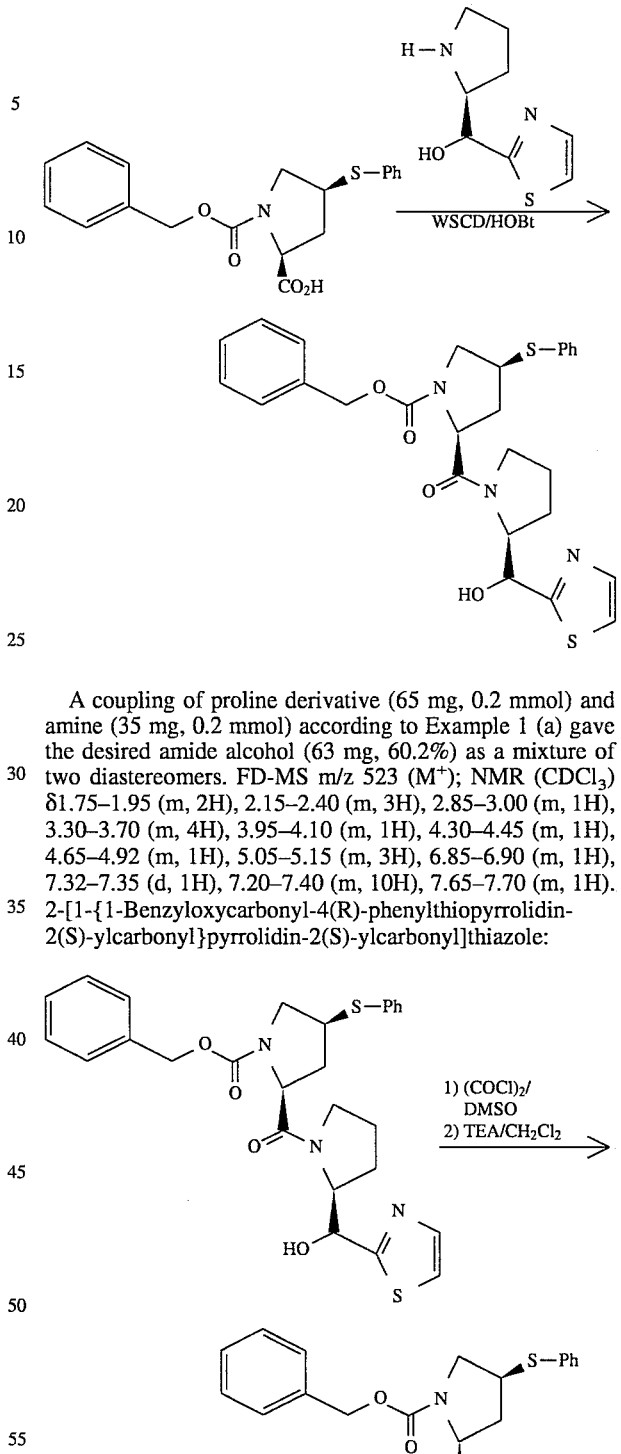

A coupling of proline derivative (65 mg, 0.2 mmol) and amine (35 mg, 0.2 mmol) according to Example 1 (a) gave the desired amide alcohol (63 mg, 60.2%) as a mixture of two diastereomers. FD-MS m/z 523 (M⁺); NMR (CDCl₃) δ1.75–1.95 (m, 2H), 2.15–2.40 (m, 3H), 2.85–3.00 (m, 1H), 3.30–3.70 (m, 4H), 3.95–4.10 (m, 1H), 4.30–4.45 (m, 1H), 4.65–4.92 (m, 1H), 5.05–5.15 (m, 3H), 6.85–6.90 (m, 1H), 7.32–7.35 (d, 1H), 7.20–7.40 (m, 10H), 7.65–7.70 (m, 1H).

2-[1-{1-Benzyloxycarbonyl-4(R)-phenylthiopyrrolidin-2(S)-ylcarbonyl}pyrrolidin-2(S)-ylcarbonyl]thiazole:

A oxidation of proline amide alcohol (50 mg, 0.1 mmol) according to Example 1(b) gave the desired ketone (39 mg, 74.9%) as white foam. FD-MS m/z 521 (M⁺); NMR (CDCl₃) δ1.92–2.46 (m, 5H), 2.66–2.74 (m, 1H), 3.37–4.10 (m, 5 H), 4.46–4.51 (m, 0.4H), 4.57–4.61 (m, 0.6 H), 4.97–5.16 (m, 2H), 5.56 (dd, 0.4H, J=4.7, 8.6 Hz), 5.78 (dd, 0.6 H, J=4.7, 8.6 Hz), 7.22–7.43 (m, 10H), 7.67 (d, 0.6 H, J=3.1 Hz), 7.69 (d, 0.4H, J=3.1 Hz), 8.00 (d, 0.6 H, J=3.1 Hz), 8.02 (d, 0.4H, J=3.1 Hz).

EXAMPLE 3

4-}1-(1-Benzyloxycarbonylindolin-2(S)-ylcarbonyl) pyrrolidin-2(S)-ylcarbonyl}oxazole (a) 4-{1-(1-Benzyloxycarbonylindolin-2(S)-ylcarbonyl)pyrrolidin2(S) -ylhyoxymethyl}oxazole:

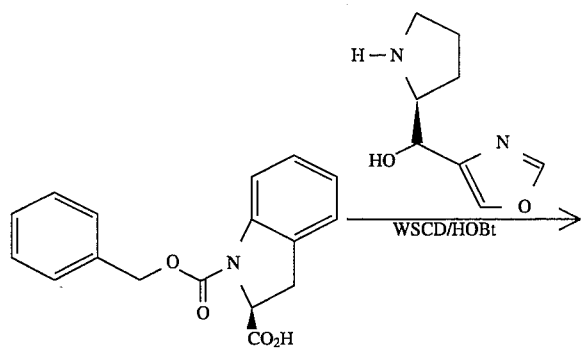

A coupling of proline derivative (60 mg, 0.2 mmol) and amine (34 mg, 0.2 mmol) according to Example 1(a) gave the desired amide alcohol (54 mg, 60.2%) as a mixture of two diastereomers. FD-MS m/z 447 (M⁺); NMR (CDCl₃) δ1.85–2.55 (m, 4H), 3.30–3.80 (m, 4H), 4.22–4.60 (m, 1H), 4.80–5.42 (m, 4H), 6.88–7.35 (m, 9H), 7.45–7.50 (m, 1H), 7.75–7.85 (m, 1H).

(b) 4-{1-(1-Benzyloxycarbonylindolin-2(S)-ylcarbonyl)pyrrolidin2(S) -ylcarbonyl}oxazole:

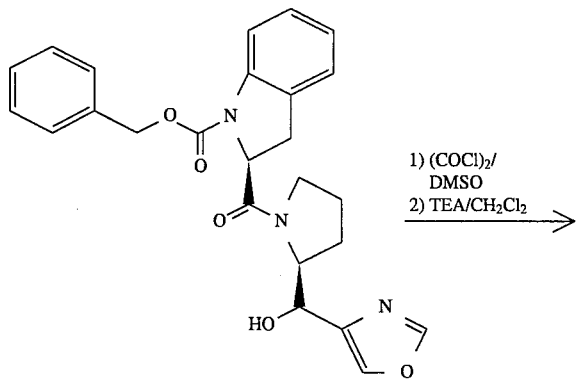

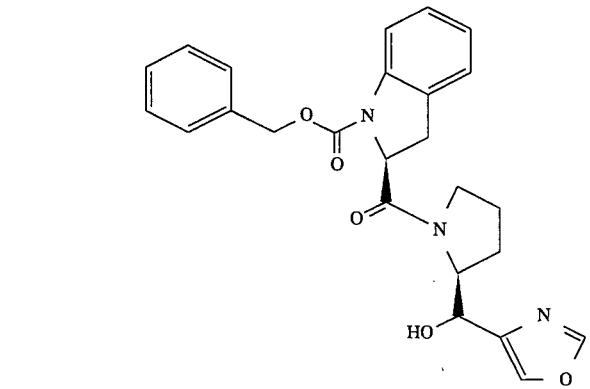

Oxidation of proline amide alcohol (46 mg, 0.1 mmol) according to Example 1(b) gave the desired ketone (46 mg, 90.2%) as white foam. FD-MS m/z 445 (M⁺); NMR (CDCl₃, 400 MHz) δ1.82–2.40 (m, 4H), 3.20–3.25 (m, 1H), 3.42–3.96 (m, 3H), 4.98–5.32 (m, 4H), 6.91–7.00 (m, 1H), 7.05–7.33 (m, 7.6H), 7.82–7.84 (m, 1.4H), 8.15–8.17 (m, 1H)

EXAMPLE 4

2-{1-(1-Benzyloxycarbonylpyrrolidin-2(S)-ylcarbonyl) pyrrolidin-2(S)-ylcarbonyl}thiazole FD-MS m/z 413 (M⁺); NMR (CDCl₃, 400 MHz) δ1.86–1.98 (m, 2H), 2.02–2.46 (m, 6H), 3.46–3.93 (m, 4H), 4.48 (dd, 0.4 H, J=3.9, 8.5 Hz), 4.61 (dd, 0.6 H, J=3.9, 8.5 Hz), 5.00–5.19 (m, 2H), 5.61 (dd, 0.4 H, J=4.6, 9.0 Hz), 5.78 (dd, 0.6 H, J=4.6, 9.0 Hz), 7.28–7.39 (m, 5H), 7.66 (d, 0.4 H, J=3.1 Hz), 7.68 (d, 0.6H, J=3.1 Hz), 8.00 (d, 0.6H, J=3.1 Hz), 8.02 (d, 0.4H, J=3.1 Hz)

EXAMPLE 5

2-[1-{1(4-Phenylbutanoyl)pyrrolidin-2(S)-ylcarbonyl} pyrrolidin-2(S)-ylcarbonyl]thiazole FD-MS m/z 425 (M⁺); NMR (CDCl₃, 400 MHz) δ1.90–2.00 (m, 4H), 2.01–2.21 (m, 5H), 2.25–2.40 (m, 2H), 2.45–2.55 (m, 1H), 2.65–2.75 (m, 2H), 3.40–3.50 (m, 1H), 3.55–3.65 (m, 1H), 3.72–3.80 (m, 1H) 4.00–5.05 (m, 1H), 4.73 {dd, 1H, J: 3.6, 8.0 I-Lz), 5.75 {dd, 1 H, J: 4.7, 9.0 Hz), 7.15–7.23 (m, 3H), 7.24–7.30 (m, 2H), 7.65 (d, 1H, J=3.1 Hz), 8.00 (d, 1H, J=3.1 Hz).

EXAMPLE 6

2-{1(1-Benzyloxycarbonyloctahydroindol-2(S)-ylcarbonyl)pyrrolidin-2(S)ylcarbonyl}thiazole FD-MS m/z 467 (M$^+$); NMR (CDCl$_3$, 400 MHz) δ1.00–1.74 (m, 8H), 1.84–2.14 (m, 6H), 2.27–2.46 (m, 1H), 3.36–3.48 (m, 1H), 3.70–3.84 (m, 1H), 3.89–4.00 (m, 1H), 4.54–4.58 (m, 1H), 4.95–5.16 (m, 2H), 5.58–5.62 (m, 0.5H), 5.82–5.86 (m, 0.5H), 7.25–7.38 (m, 5H), 7.65–7.67 (m, 1H), 8.00–8.02 (m, 1H).

EXAMPLE 7

2-[1-{1-(4-Phenylbutanoyl)octahydroindol-2(S)-ylcarbonyl}pyrrolidin-2(S)-ylcarbonyl]thiazole FD-MS m/z 479 (M$^+$); NMR (CDCl$_3$, 400 MHz) δ1.05–1.80 (m, 8H), 1.91–2.11 (m, 7H), 2.22–2.30 (m, 3H), 2.42–2.59 (m, 1H), 2.57–2.66 (m, 2H), 3.58–3.73 (m, 2H), 4.02–4.07 (m, 1H), 4.60–4.64 (m, 1H), 5.80–5.83 (m, 1H), 7.14–7.27 (m, 5H), 7.63 (d, 1H, J=3.1 Hz), 7.98 (d, 1H, J=3.1 Hz).

EXAMPLE 8

2-{1-(1-Benzyloxycarbonylindolin-2(S)-ylcarbonyl)pyrrolidin-2(S)-ylcarbonyl}thiazole FD-MS m/z 461 (M$^+$); NMR (CDCl$_3$, 400 MHz) δ1.95–2.47 (m, 4H), 3.21–3.96 (m, 4H), 5.00–5.39 (m, 3H), 5.63–5.83 (m, 1H), 6.91–7.00 (m, 2H), 7.06–7.91 (m, 7H), 7.67 (d, 1H, J=3.1 Hz), 8.01 (d, 1H, J=3.1 Hz).

EXAMPLE 9

2-[1-{1-(4-Phenylbutanoyl)indolin-2(S)-ylcarbonyl}pyrrolidin-2(S)-ylcarbonyl]thiazole FD-MS m/z 473 (M$^+$); NMR (CDCl$_3$, 400 MHz) δ2.00–2.27 (m, 6H), 2.41–2.45 (m, 1H), 2.67–2.77 (m, 3H), 3.16–4.05 (m, 4H), 4.87–4.90 (m, 0.4H), 5.32–5.36 (m, 0.6H), 5.71–5.79 (m, 1H), 6.90–7.00 (m, 2H), 7.10–7.29 (m, 7H), 7.63–7.67 (m, 1H), 7.97–8.01 (m, 1H).

EXAMPLE 10

2-[1-{1-(4-Phenylbutanoyl)-4(R)-phenylthiopyrrolidin-2(S)-ylcarbonyl}-pyrrolidin-2(S)-ylcarbonyl]thiazole.

FD-MS m/z 533 (M$^+$); NMR (CDCl$_3$, 400 MHz) δ1.90–2.13 (m, 7H), 2.21–2.25 (m, 2H), 2.39–2.46 (m, 1H), 2.60–2.72 (m, 2H), 3.41–3.46 (m, 1H), 3.55–3.59 (m, 1H), 3.61–3.69 (m, 1H), 3.78–3.82 (m, 1H), 3.95–4.00 (m, 1H), 4.66 (t, 1H, J=8.3 Hz) 5.75 (dd, 1H, J=4.6, 9.0 Hz), 7.13–7.22 (m, 3H), 7.23–7.35 (m, 5H), 7.41–7.43 (m, 2H), 7.66 (d, 1H, J=3.1 Hz), 7.99 (d, 1H, J=3.1 Hz).

EXAMPLE 11

2-[1-{1-(4-Phenylbutanoyl)piperidin-2(S)-ylcarbonyl}pyrrolidin-2(S)-ylcarbonyl]thiazole FD-MS m/z 439 (M$^+$); NMR (CDCl$_3$) δ1.37–2.72 (m, 16H), 3.40–3.87 (m, 4H), 5.39–5.53 (m, 1H), 5.66–5.71 (m, 1H), 7.17–7.30 (m, 5H), 7.67 (d, 1H, J=3.06 Hz), 8.00 (d, 1H, J=3.06 Hz).

EXAMPLE 12

2-[1-{2-(4-Phenylbutanoyl)-1,2,3,4-tetrahydroisoquinolin-3-ylcarbonyl}pyrrolidin-2(S)-ylcarbonyl]thiazole FD-MS m/z 487 (M$^+$); NMR (CDCl$_3$) δ1.90–2.08 (m, 10H), 3.03–3.19 (m, 2H), 3.64–3.77 (m, 2H), 4.62 (ABq, 2H, J=43.5, 16.3 Hz), 5.67 (m, 1H), 5.76 (m, 1H), 7.12–7.29 (m, 9H), 7.63 (d, 1H, J=3.0 Hz), 7.96 (d, 1H, J=3.0 Hz).

EXAMPLE 13

2-[1-{3-(4-Phenylbutanoyl)thiazolin-4(R)-ylcarbonyl}pyrrolidin-2(S)-ylcarbonyl]thiazole FD-MS m/z 443 (M$^+$); NMR (CDCl$_3$) δ1.96–2.68 (m, 10H), 3.19–3.39 (m, 2H), 3.70–4.05 (m, 2H), 4.55 (ABq, 2H, J=16.6, 8.9 Hz), 5.13 (m, 1H), 5.73 (m, 1H), 7.15–7.28 (m, 5H), 7.67 (d, 1H, J=2.95 Hz), 8.00 (d, 1H, J=2.95 Hz).

EXAMPLE 14

2-[1-{3-(4-Phenylbutanoyl)-2(S)-phenylthiazolin-4(R)-ylcarbonyl}pyrrolidin-2(S)-ylcarbonyl]thiazole FD-MS m/z 519 (M$^+$); NMR (CDCl$_3$) δ1.76–2.51 (m, 10H), 3.25–3.54 (m, 2H), 3.74–3.98 (m, 2H), 5.40 (m, 1H), 5.79 (m, 1H), 6.03 (s, 1H), 6.98–7.35 (m, 10H), 7.67 (d, 1H, J=2.94 Hz), 7.99 (d, 1H, J=2.94 Hz).

EXAMPLE 15

2-[1-{2-Benzylthioacetylcyclopentan-1-ylcarbonyl)pyrrolidin-2(S)-ylcarbonyl}thiazole FD-MS m/z 412 (M$^+$): NMR (CDCl$_3$) δ1.59–2.08 (m, 8H), 2.10–2.38 (m, 2H), 3.15–3.28 (m, 1H), 3.40–3.45 (m, 1H), 3.61–3.79 (m, 4H), 3.95–4.05 (m, 1H), 4.12–4.18 (m, 1H), 5.65–5.69 (m, 1H), 7.19–7.28 (m, 5H) 7.66–7.67 (d, 1H, J=3.05 Hz), 7.99–8.00 (d, 1H, J=3.05 Hz).

EXAMPLE 16

2-[1-(2-Benzylthioacetylcyclohexan-1-ylcarbonyl)pyrrolidin-2(S)-ylcarbonyl]thiazole FD-MS m/z 456 (M$^+$); NMR (CDCl$_3$) δ1.22–1.38 (m, 5H), 1.57–2.11 (m, 7H), 2.36–2.43 (m, 1H), 2.74–2.79 (m, 1H), 3.07–3.13 (m, 1H), 3.21–3.32 (m, 2H), 3.60–3.67 (m, 2H), 3.71–3.76 (m, 1H), 3.83–3.89 (m, 1H), 5.60–5.62 (m, 1H), 7.19–7.27 (m, 5H), 7.64–7.65 (d, 1H, J=2.82 Hz), 7.97–7.98 (d, 1H, J=2.82 Hz).

EXAMPLE 17

2-{1-(1-Benzyloxycarbonylpyrrolidin-2(S)-ylcarbonyl)pyrrolidin-2(S)-ylcarbonyl}benzothiazole FD-MS m/z 463 (M$^+$); $^1$H-NMR (CDCl$_3$, 400 MHz) δ1.83–2.20 (m, 6H), 2.22–2.26 (m, 1H), 2.40–2.48 (m, 1H), 3.43–3.98 (m, 4H), 4.48–4.63 (m, 1H) 5.01–5.18 (m, 2H), 5.68 (dd, 0.4H, J=4.7, 8.9 Hz), 5.89 (dd, 0.6H, J=4.7, 8.9 Hz), 7.27–7.34 (m, 5H), 7.49–7.59 (m, 2H), 7.96–7.98 (m, 1H), 8.16–8.20 (m, 1H).

EXAMPLE 18

2-{1-(1-Benzyloxycarbonylindolin-2(S)-ylcarbonyl)pyrrolidin-2(S)-ylcarbonyl}benzothiazole FD-MS m/z 511 (M$^+$); $^1$H-NMR (CDCl$_3$, 400 MHz) δ2.00–2.45 (m, 4H), 3.21–3.26 (m, 1H), 3.47–4.10 (m, 3H), 5.06–5.39 (m, 3H), 5.73–5.76 (m, 0.6H), 5.93–5.96 (m, 0.4H), 6.90–7.16 (m, 2H), 7.18–7.42 (m, 6.6H) 7.50–7.58 (m, 2H), 7.88–7.90 (m, 0.4H), 7.94–7.96 (m, 1H), 8.18–8.20 (m, 1H).

EXAMPLE 19

2-[1-{1-(4-Phenylbutanoyl)indolin-2(S)-ylcarbonyl}pyrrolidin-2(S)-ylcarbonyl]benzothiazole FD-MS m/z 523 (M$^+$); NMR (CDCl$_3$, 400 MHz) δ2.00–2.30 (m, 6H), 2.43–2.54 (m, 1H), 2.64–2.78 (m, 3H), 3.15–4.08 (m, 4H), 4.90–4.91 (m, 0.4H), 5.34 (dd, 0.6H, J=3.6, 8.1 Hz), 5.83–5.85 (m, 0.4H), 5.88 (dd, 0.6H, J=4.6, 8.9 Hz), 6.91–7.07 (m, 2H), 7.11–7.32 (m, 6.6H), 7.49–7.56 (m, 2H), 7.92–7.96 (m, 1H), 8.14–8.19 (m, 1H), 8.25–8.27 (m, 0.4H).

EXAMPLE 20

2-{1-(1-Benzyloxycarbonyl-4(R)-phenylthiopyrrolidin-2(S)-ylcarbonyl)pyrrolidin-2(S)-ylcarbonyl}benzothiazole.

FD-MS m/z 571 (M$^+$); NMR (CDCl$_3$, 400 MHz) δ1.90–2.17 (m, 4H), 2.45–2.51 (m, 1H), 2.64–2.75 (m, 1H), 3.38–3.73 (m, 4H), 3.92–4.11 (m, 1 H), 4.47–4.62 (m, 1H), 4.98–5.16 (m, 2H), 5.66 (dd, 0.4H, J=5.0, 8.6 Hz), 5.90 (dd, 0.6H, J=5.0, 8.6 Hz), 7.19–7.40 (m, 10H), 7.50–7.60 (m, 2H), 7.97–7.99 (m, 1H), 8.15–8.20 (m, 1H).

EXAMPLE 21

2-[1-{1-(4-Phenylbutanoyl)-4(R)-phenylthiopyrrolidin-2(S)-ylcarbonyl}pyrrolidin-2(S)-ylcarbonyl]benzothiazole FD-MS m/z 583 (M$^+$); NMR (CDCl$_3$, 400 MHz) δ1.92–2.24 (m, 7H), 2.48–2.51 (m, 1H), 2.60–2.70 (m, 4H), 3.43–3.81 (m, 4H), 3.98–4.02 (m, 1H), 4.64–4.68 (m, 1H), 5.85–5.89 (m, 1H), 7.13–7.41 (m, 10H), 7.50–7.58 (m, 2H), 7.96–7.98 (m, 1H), 8.15–8.17 (m, 1H).

EXAMPLE 22

2-[1-(2-Benzylthioacetylcyclohexan-1-ylcarbonyl)pyrrolidin-2(S)-ylcarbonyl]benzothiazole FD-MS m/z 506 (M$^+$); NMR (CDCl$_3$) δ1.25–1.39 (m, 5H), 1.81–2.15 (m, 7H), 2.42–2.49 (m, 1H), 2.75–2.80 (m, 1H), 3.07–3.13 (m, 1H), 3.21–3.32 (m, 2H), 3.74–3.80 (m, 1H), 3.88–3.91 (m, 1H), 5.69–5.73 (m, 1H), 7.16–7.28 (m, 5H), 7.48–7.56 (m, 2H), 7.95–7.97 (m, 1H), 8.12–8.14 (m, 1H).

EXAMPLE 23

2-[1-{1-(4-Phenylbutanoyl)pyrrolidin-2(S)-ylcarbonyl}pyrrolidin-2(S)-ylcarbonyl]oxazole FD-MS m/z 409 (M$^+$); NMR (CDCl$_3$, 400 MHz) δ1.89–2.00 (m, 5H), 2.04–2.17 (m, 4H), 2.22–2.36 (m, 3H), 2.63–2.67 (m, 2H), 3.36–3.42 (m, 1H), 3.53–3.66 (m, 1H), 3.68–3.72 (m, 1H), 3.93–3.99 (m, 1H), 4.72 (dd, 1H, J=3.5, 7.8 Hz), 5.40 (dd, 1H, J=4.7, 8.6 Hz), 7.14–7.24 (m, H), 7.25–7.27 (m, 3H), 7.88 (d, 1H, J=1.2 Hz), 8.29 (d, 1H, J=1.2 Hz).

EXAMPLE 24

2-[1-{1-(4-Phenylbutanoyl)indolin-2(S)-ylcarbonyl}pyrrolidin-2(S)-ylcarbonyl]oxazole FD-MS m/z 457 (M$^+$); NMR (CDCl$_3$, 400 MHz) δ1.95–2.39 (m, 7H), 2.67–2.74 (m, 3H), 3.14–4.02 (m, 4H), 4.86–5.31 (m, 2H), 6.95–7.00 (m, 2H), 7.11–7.29 (m, 6.6H), 7.89–7.91 (m, 1H), 8.24–8.25 (m, 1.4H).

EXAMPLE 25

4-{1-(1-Benzyloxycarbonylpyrrolidin-2(S)-ylcarbonyl)pyrrolidin-2(S)-ylcarbonyl}thiophene FD-MS m/z 412 (M$^+$); NMR (CDCl$_3$, 400 MHz) δ1.90–2.20 (m, 6H), 2.20–2.30 (m, 2H), 3.47–3.89 (m, 4H), 4.48 (dd, 0.4H, J=3.6, 8.3 Hz), 4.59 (dd, 0.6H, J=3.6, 8.3 Hz), 4.99–5.19 (m, 2H), 5.44 (dd, 1 H, J=4.2, 8.9 Hz), 7.12–7.14 (m, 1H), 7.14–7.30 (m, 5H), 7.63–7.65 (m, 1H), 7.77–7.82 (m, 1H).

EXAMPLE 26

2-[1-{1-(4-Phenylbutanoyl)pyrrolidin-2(S)-ylcarbonyl}pyrrolidin-2(S)-ylcarbonyl]thiophene FD-MS m/z 424 (M$^+$); NMR (CDCl$_3$, 400 MHz) δ1.90–2.01 (m, 5H), 2.06–2.13 (m, 4H), 2.20–2.32 (m, 3H), 2.64–2.68 (m, 2H), 3.39–3.56 (m, 2H), 3.67–3.73 (m, 1H), 3.91–3.97 (m, 1H), 4.72 (dd, 1H, J=3.6, 7.8 Hz), 5.41 (dd, 1H, J=4.2, 8.8 Hz), 7.23–7.27 (m, 5H), 7.12 (dd, 1H, J =3.9, 5.0 Hz), 7.63 (dd, 1H, J=1.1, 5.0 Hz), 7.80 (dd, 1H, J=1.1, 3.9 Hz).

EXAMPLE 27

4,5-Dimethyl-2-[1-{1-(4-phenylbutanoyl)pyrrolidin-2(S)-ylcarbonyl}pyrrolidin-2(S)-ylcarbonyl]thiazole FD-MS m/z 453(M$^+$); NMR (CDCl$_3$, 400 MHz) δ1.90–2.00 (m, 4H), 2.05–2.17 (m, 5H), 2.27–2.33 (m, 1H), 2.31–2.43 (m, 2H), 2.36 (s, 3H), 2.41 (s, 3H), 2.64–2.67 (m, 2H), 3.35–3.40 (m, 1H), 3.53–3.55 (m, 1H), 3.65–3.71 (m, 1H), 3.94–4.00 (m, 1H), 4.73 (dd, 1H, J=3.6, 7.4 Hz), 5.72 (dd, 1H, J=5.1, 9.0 Hz), 7.14–7.27 (m, 5H).

EXAMPLE 28

2-[1-{1-(4-Phenylbutanoyl)pyrrolidin-2(S)-ylcarbonyl}pyrrolidin-2(S)-ylcarbonyl]-1H-imidazole FD-MS m/z 408 (M$^+$); NMR (CDCl$_3$, 400 MHz) δ1.92–2.10 (m, 8H), 2.14–2.33 (m, 3H), 2.42–2.45 (m, 1H), 2.66–2.70 (m, 2H), 3.39–3.45 (m, 1H), 3.56–3.61 (m, 1H), 3.70–3.74 (m, 1H), 3.98–4.02 (m, 1H), 4.86 (d, 1H, J=3.9 Hz), 5.64 (d, 1H, J=4.7 Hz), 7.07 (br.s, 1H), 7.12 (br.s, 1H), 7.15–7.32 (m, 5H).

EXAMPLE 29

2-[1-{1-(4-Phenylbutanoyl)pyrrolidin-2(S)-ylcarbonyl}pyrrolidin-2(S)-ylcarbonyl]-1H-benzimidazole FD-MS m/z 458 (M$^+$); NMR (CDCl$_3$, 400 MHz) δ2.03–2.15 (m, 3H), 2.16–2.30 (m, 6H), 2.31–2.39 (m, 2H), 2.59–2.62 (m, 1H), 2.72–2.76 (m, 2H), 3.45–3.49 (m, 1H), 3.61–3.63 (m, 1H), 3.84–3.88 (m, 1H), 4.12–4.16 (m, 1H), 4.86–4.89 (m, 1H), 5.85 (dd, 1H, J=5.4, 9.0 Hz), 7.21–7.34 (m, 5H), 7.37–7.45 (m, 2H), 7.56 (d, 1H, J=8.0 Hz), 7.83 (d, 1H, J=8.0 Hz).

EXAMPLE 30

3-[1-{1-(4-Phenylbutanoyl)pyrrolidin-2(S)-ylcarbonyl}pyrrolidin-2(S)-ylcarbonyl]pyridine FD-MS m/z 419(M$^+$); $^1$H-NMR (CDCl$_3$, 400 MHz) δ1.87–2.04 (m, 5H), 2.05–2.20 (m, 4H), 2.25–2.35 (m, 3H), 2.65–2.68 (m, 2H), 3.41–3.55 (m, 1H), 3.54–3.59 (m, 1H), 3.70–3.76 (m, 1H), 3.96–4.02 (m, 2H), 4.70 (dd, 1H, J=3.6, 7.7 Hz), 5.49 (dd, 1H, J=3.6, 7.7 Hz), 7.14–7.29 (m, 5H), 7.46–7.48 (m, 1H), 8.34 (m, 1H), 8.78 (m, 1H), 9.19 (br.s, 1H).

EXAMPLE 31

5-[1-{1-(4-Phenylbutanoyl)pyrrolidin-2(S)-ylcarbonyl}pyrrolidin-2(S)-ylcarbonyl]pyrimidine FD-MS m/z 420(M$^+$); $^1$H-NMR (CDCl$_3$, 400 MHz) δ1.87–2.05 (m, 5H), 2.08–2.21 (m, 4H), 2.25–2.37 (m, 3H), 2.64–2.68 (m, 2H), 3.39–3.44 (m, 1H), 3.53–3.59 (m, 1H), 3.70–3.76 (m, 1H), 3.98–4.04 (m, 1H), 4.68–4.70 (m, 1H), 5.43 (dd, 1H, J=4.9, 8.7 Hz), 7.15–7.24 (m, 3H), 7.26–7.28 (m, 2H), 9.26 (s, 2H), 9.35 (s, 1H).

EXAMPLE 32

2-[1-{1-(4-Phenylbutanoyl)pyrrolidin-2(S)-ylcarbonyl}pyrrolidin-2(S)-ylcarbonyl]pyridine FD-MS m/z 419(M$^+$); $^1$H-NMR (CDCl$_3$, 400 MHz) δ1.93–2.03 (m, 4H), 2.05–2.21 (m, 5H), 2.23–2.37 (m, 2H), 2.40–2.48 (m, 1H), 2.63–2.67 (m, 2H), 3.37–3.43 (m, 1H), 3.53–3.57 (m, 1H), 3.68–3.74 (m, 1H), 3.97–4.02 (m, 1H), 4.75 (dd, 1H, J=3.3, 7.4 Hz), 5.98 (dd, 1H, J=4.9, 9.0 Hz), 7.14–7.23 (m, 3H), 7.24–7.29 (m, 2H), 7.43 (ddd, 1H, J=0.8, 4.9, 7.7 Hz), 7.78 (ddd, 1H, J=1.56, 7.7, 7.7 Hz), 8.02 (d, 1H, J=7.7 Hz), 8.65 (d, 1H, J=4.9 Hz).

EXAMPLE 33

5-[1-{1-(4-Phenylbutanoyl)pyrrolidin-2(S)-ylcarbonyl}pyrrolidin-2(S)-ylcarbonyl]thiazole FD-MS m/z 425(M$^+$); $^1$H-NMR (CDCl$_3$, 400 MHz) δ1.91–2.06 (m, 4H), 2.09–2.24 (m, 4H), 2.27–2.34 (m, 3H), 2.62–2.68 (m, 3H), 3.40–3.42 (m, 1H), 3.54–3.56 (m, 1H), 3.68–3.73 (m, 1H), 3.94–4.00 (m, 1H), 4.70 (dd, 1H, J=3.6, 8.0 Hz), 5.33 (dd, 1H, J=4.6, 8.7 Hz), 7.15–7.24 (m, 3H), 7.25–7.27 (m, 2H), 8.54 (s, 1H), 9.00 (s, 1H), 8.65–8.67 (m, 1H).

EXAMPLE 34

3-[1-{1-(4-Phenylbutanoyl)pyrrolidin-2(S)-ylcarbonyl}pyrrolidin-2(S)-ylcarbonyl]1,2,4-triazole FD-MS m/z 409(M$^+$); $^1$H-NMR (CDCl$_3$, 400 MHz) δ1.94–211 (m, 4H), 2.12–2.32 (m, 5H), 2.34–2.37 (m, 3H), 2.62–2.66 (m, 2H), 3.42–3.44 (m, 1H), 3.54–3.64 (m, 1H), 3.73–3.76 (m, 1H), 3.94–3.96 (m, 1H), 4.72 (d, 1H, J=5.6 Hz), 5.76 (br.s, 1H), 7.14–7.31 (m, 5H), 8.31 (br.s, 1H).

EXAMPLE 35

2-[1-{1-(4-Phenylbutanoyl)pyrrolidin-2(S)-ylcarbonyl}pyrrolidin-2(S)-ylcarbonyl]pyrazole FD-MS m/z 408(M$^+$); $^1$H-NMR (CDCl$_3$, 400 MHz) δ1.91–2.03 (m, 7H), 2.04–2.20 (m, 1H), 2.25–2.38 (m, 3H), 2.64–2.67 (m, 2H), 3.39–3.43 (m, 1H), 3.56–3.58 (m, 1H), 3.67–3.73 (m, 1H), 3.92–3.98 (m, 1H), 4.75 (dd, 1H, J=3.6, 7.8 Hz), 5.74–5.76 (m, 1H), 6.74 (d, 1H, J=2.2 Hz), 7.14–7.23 (m, 3H), 7.24–7.30 (m, 2H), 7.43 (d, 1H, J=2.2 Hz).

EXAMPLE 36

2-[1-{1-(4-Phenylbutanoyl)pyrrolidin-2(S)-ylcarbonyl}pyrrolidin-2(S)-ylcarbonyl]benzoxazole FD-MS m/z 459(M$^+$); $^1$H-NMR (CDCl$_3$, 400 MHz) δ1.93–2.03 (m, 4H), 2.04–2.17 (m, 5H), 2.21–2.34 (m, 2H), 2.42–2.49 (m, 1H), 2.63–2.67 (m, 2H), 3.35–3.40 (m, 1H), 3.51–3.56 (m, 1H), 3.75–3.79 (m, 1H), 4.02–4.06 (m, 1H), 4.72–4.75 (m, 1H), 5.73 (dd, 1H, J=5.4, 8.5 Hz), 7.14–7.31 (m, 5H), 7.42–7.46 (m, 1H), 7.49–7.54 (m, 1H), 7.62–7.64 (m, 1H), 7.86–7.88 (m, 1H).

EXAMPLE 37

2-[1-{1-(4-Phenylbutanoyl)pyrrolidin-2(S)-ylcarbonyl}pyrrolidin-2(S)-ylcarbonyl]oxazolo[4,5-b]pyridine FD-MS m/z 460(M$^+$); $^1$H-NMR (CDCl$_3$, 400 MHz) δ1.88–2.32 (m, 11H), 2.47–2.53 (m, 1H), 2.63–2.67 (m, 2H), 3.35–3.40 (m, 1H), 3.51–3.56 (m, 1H), 3.75–3.79 (m, 1H), 4.02–4.06 (m, 1H), 4.72 (dd, 1H. J=3.0, 8.4 Hz), 5.61 (dd, 1H, J=5.9, 8.2 Hz), 7.14–7.30 (m, 5H), 7.48 (dd, 1H, J=4.9, 8.5 Hz), 7.98 (dd, 1H, J=1.5, 8.5 Hz), 8.74 (dd, 1H, J=1.5, 4.9 Hz).

EXAMPLE 38

2-[1-{1-(4-Phenylbutanoyl)pyrrolidin-2(S)-ylcarbonyl}pyrrolidin-2(S)-ylcarbonyl]imidazo[4,5-b]pyridine FD-MS m/z 459(M$^+$); $^1$H-NMR (CDCl$_3$, 400 MHz) δ1.87–2.04 (m, 3H), 2.05–2.22 (m, 6H), 2.26–2.29 (m, 2H), 2.33–2.50 (m, 1H), 2.62–2.66 (m, 2H), 3.36–3.41 (m, 1H), 3.51–3.59 (m, 1H), 3.79–3.84 (m, 1H), 4.05–4.11 (m, 1H), 4.77–4.80 (m, 1H), 5.82 (br. s, 1H), 7.12–7.26 (m, 5H), 7.35 (dd, 1H, J=4.9, 8.2 Hz), 8.22 (dd, 1H, J=1.3, 8.2 Hz), 8.78 (dd, 1H, J=1.3, 4.9 Hz).

EXAMPLE 39

2-{1-{1-Benzyloxycarbonyl)pyrrolidin-2(S)-ylcarbonyl)pyrrolidin-2(S)-ylcarbonyl}benzimidazole FD-MS m/z 446(M$^+$); $^1$H-NMR (CDCl$_3$, 400 MHz) δ1.80–1.87 (m, 2H), 1.95–2.03 (m, 1H), 2.05–2.50 (m, 5H), 3.45–3.65 (m, 3H), 3.73–3.80 (m, 0.4H), 3.95–3.99 (m, 0.6H), 5.03–5.17 (m, 2H), 4.54 (dd, 0.4H, J=3.8, 7.2 Hz), 4.66 (dd, 0.6H, J=3.8, 8.6 Hz), 5.69 (dd, 0.4H, J=5.1, 8.4 Hz), 5.79 (dd, 0.6H, J=5.1, 8.7 Hz), 7.24–733 (m, 7H), 7.36–7.52 (brs, 2H).

EXAMPLE 40

2-Methoxy-3-[1-{1-(4-phenylbutanoyl)pyrrolidine-2(S)-ylcarbonyl}pyrrolidin-2(S)-ylcarbonyl]pyrazine FD-MS m/z 450(M$^+$); $^1$H-NMR (CDCl$_3$, 400 MHz) δ1.89–2.19 (m, 9H), 2.21–2.36 (m, 3H), 2.63–2.67 (m, 2H), 3.36–3.40 (m, 1H), 3.53–3.58 (m, 1H), 3.67–3.72 (m, 1H), 3.91–3.97 (m, 1H), 4.05 (s, 3H), 4.72–4.75 (m, 1H), 5.89 (dd, 1H, J=4.7, 8.8 Hz), 7.14–7.27 (m, 5H), 8.22 (d, 1H, J=2.5 Hz), 8.27 (d, 1H, J=2.5 Hz).

EXAMPLE 41

2-[1-{1-(4-Phenylbutanoyl)pyrrolidin-2(S)-ylcarbonyl}pyrrolidin-2(S)-ylcarbonyl]thiazoline FD-MS m/z 427(M$^+$); $^1$H-NMR (CDCl$_3$, 400 MHz) δ1.89–2.18 (m, 10H), 2.21–2.33 (m, 2H), 2.64–2.68 (m, 2H), 3.27–3.32 (m, 2H), 3.36–3.42 (m, 1H), 3.55–3.66 (m, 2H), 3.88–3.94 (m, 1H), 4.43–4.59 (m, 2H), 4.69 (dd, 1H, J=3.6, 8.0 Hz), 5.47 (dd, 1H, J=5.0, 8.8 Hz), 7.15–7.28 (m, 5H).

TABLE 1

PEP Inhibitory Activity of Pyrrolidin-2-ylcarbonylheterocyclic Compounds.

| Example No. | IC$_{50}$(ng/ml) | Example No. | IC$_{50}$(ng/ml) |
|---|---|---|---|
| 1 | 1.02 | 26 | 810 |
| 2 | 2.50 | 27 | 2.75 |
| 3 | 4.25 | 28 | 2.55 |
| 4 | 2.40 | 29 | 1.75 |
| 5 | 1.33 | 30 | 1100 |
| 6 | 2.00 | 31 | 27.0 |
| 7 | 1.15 | 32 | 3.0 |
| 8 | 1.70 | 33 | 275 |
| 9 | 2.60 | 34 | 2.50 |
| 10 | 0.60 | 35 | 46.0 |
| 15 | 24.0 | 36 | 1.90 |
| 16 | 24.5 | 37 | 2.20 |
| 17 | 1.75 | 38 | 2.80 |

TABLE 1-continued

PEP Inhibitory Activity of Pyrrolidin-2-ylcarbonylheterocyclic Compounds.

| Example No. | IC$_{50}$(ng/ml) | Example No. | IC$_{50}$(ng/ml) |
|---|---|---|---|
| 18 | 3.75 | 39 | 3.40 |
| 19 | 2.85 | 40 | 15.0 |
| 20 | 1.40 | 41 | 1.70 |
| 21 | 1.05 | Z-Pro Prolinal | 4.95 |
| 22 | 6.40 | SUAM-1221 | 14.5 |
| 23 | 3.20 | | |
| 24 | 5.50 | | |
| 25 | 570 | | |

PHARMACEUTICAL EXAMPLE

When the compounds and their acid salts of the present invention are used as the medicaments, they can be orally or parenterally administered alone or in a form of powders, granules, tablets, capsules, injections and so on. Appropriate additives such as carriers, excipients, diluents and the like can be used with the effective amount of the compound for the formulation. In the solid formulation, the compound can be mixed with appropriate pharmaceutically acceptable excipients such as bulking agents, disintegrants, lubricants and binding agents as exemplified below. Pharmaceutical composition

| | |
|---|---|
| Compound of Example | 10.0 mg |
| Lactose | 55.0 mg |
| Corn starch | 15.5 mg |
| Fine crystalline cellulose | 15.0 mg |
| Talk | 4.0 mg |
| Magnesium stearate | 0.5 mg |

After compound of Example, lactose, corn starch and fine crystalline cellulose are mixed, a binder of 5% corn starch is added. The mixture is granulated and dried. Talk and magnesium stearate are mixed with granules and the mixture is formulated into tablets.

While the dosage varies depending upon the objective disease symptom and the formulation, the daily dosage is usually in the range from 1 to 2000 mg per human adult in the case of oral administration. It is understood that dosages of the administered compositions will vary depending upon the organism or patient treated or the complexity or severity of the cognitive disorder and that it is well within the preview of an ordinarily skilled artisan or medical doctor or veterinarian to determine the suitable dosage without undue experimentation. Applicants are therefore not limited to the particular dosages recited herein.

In each case, a physician or veterinarian will administer a pharmaceutically effective amount of the compounds or compositions claimed in the instant invention to a patient in need of treatment thereof. A pharmaceutically effective amount is defined as the dosage of claimed compound or composition which is necessary to treat, alleviate or prevent the condition such as amnesia or memory loss. It is further defined to mean the dose or dosages necessary to inhibit the enzyme prolylendopeptidase.

From the results of the experiment as shown above, compounds of the present invention exhibit excellent prolyl endopeptidase inhibitory activity and thus are useful for the prevention and treatment of amnesia. The previous examples illustrate the compounds and compositions of the present invention and uses thereof. These examples should not be construed to limit the invention which is set forth in the following claims.

What is claimed is:

1. A pyrrolidin-2-ylcarbonylheterocyclic compound of the formula:

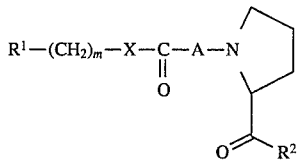

or its salt, wherein:

R¹ is aryl;

R² is a radical selected from the group consisting of 2-thiazole, 2-oxazole, 2-imidazole, 2-pyrrole, 2-thiophene, 2-benzothiazole, 2-benzoxazole, 2-benzimidazole, 4-oxazole, 2-(3,4-dimethylthiazole), 2-indole, 5-thiazole, 2-thiazoline, 2-triazole and 2-pyrazole;

X is O, thiomethylene, or CH₂;

A is:

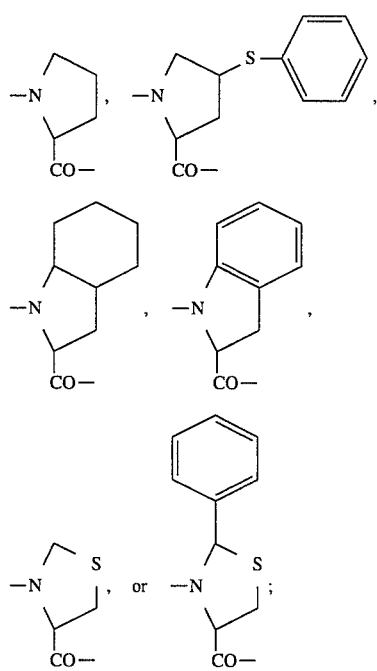

and m is an integer from 1 to 5.

2. A pyrrolidin-2-ylcarbonylheterocyclic compound of the formula:

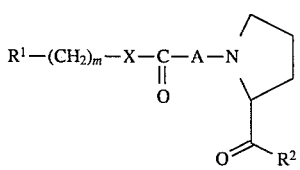

or its salt, wherein:

R¹ is aryl;

R² is a radical from the group consisting of 2-thiazole, 2-oxazole, 2-benzothiazole, 2-imidazole, 2-thiophene, 2-(3,4-dimethylthiazole), 2-benzoxazole, 2-benzimidazole, 2-indole, 5-thiazole, 2-thiazoline, 2-triazole or 2-pyrazole;

X is O, thiomethylene, or CH₂;

A is:

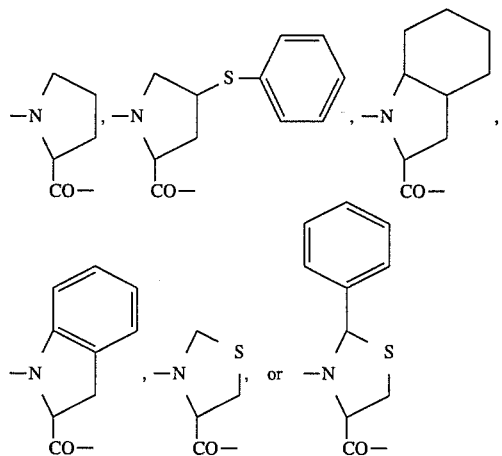

and m is an integer of from 1 to 5.

3. A pyrrolidin-2-ylcarbonylheterocyclic compound of the formula:

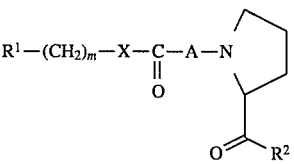

or its salt, wherein:

R¹ is aryl;

R² is a radical selected from the group consisting of 2-thiazole, 2-oxazole, 2-benzothiazole, 2-imidazole, 2-thiophene, 2-(3,4-dimethylthiazole), 2-benzoxazole, 2-benzimidazole, 2-indole, 5-thiazole, 2-thiazoline, 2-triazole or 2-pyrazole;

X is O, thiomethylene, or CH₂;

A is:

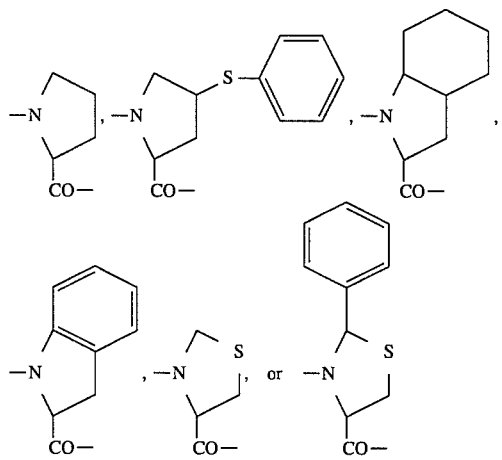

and m is an integer from 1 to 2, and wherein said compound is:

2-[1-{1-(4-phenylbutanoyl)pyrrolidin-2(S)-ylcarbonyl}pyrrolidin-2(S)-ylcarbonyl]benzothiazole, 2-[1-{1-benzyloxycarbonyl-4(R)-phenylthiopyrrolidin-2(S)-ylcarbonyl}pyrrolidin-2(S) -ylcarbonyl] thiazole, 4-{1-(1-benzyloxycarbonylindolin-2(S)-ylcarbonyl)pyrrolidin-2(S)-ylcarbonyl}oxazole, 2-{1-(1-benzyloxycarbonylpyrrolidin-2(S)-ylcarbonyl)pyrrolidin-2(S)-ylcarbonyl}thiazole, 2-[1-{1-(4-phenylbutanoyl)pyrrolidin-2(S)-ylcarbonyl}pyrrolidin-2(S)-ylcarbonyl]thiazole, 2-{1-(1-benzyloxycarbonyloctahydroindol-2(S)-ylcarbonyl)pyrrolidin-2(S)-ylcarbonyl}thiazole, 2-[1-{1-(4-phenylbutanoyl)octahydroindole-2(S)-ylcarbonyl}pyrrolidin-2(S)-ylcarbonyl]thiazole, 2-{1-(1-benzyloxycarbonyl)indolin-2(S)-ylcarbonyl)pyrrolidin-2(S)-ylcarbonyl}thiazole, 2-[1-{1-(4-phenylbutanoyl)indolin-2(S)-ylcarbonyl}pyrrolidin-2(S)-ylcarbonyl]thiazole, 2-[1-{1-(4-phenylbutanoyl)-4(R)-phenylthiopyrrolidin-2(S)-ylcarbonyl}pyrrolidin-2 (S)-ylcarbonyl] thiazole, 2-[1-{3-(4-phenylbutanoyl)thiazolin-4(R)-ylcarbonyl}pyrrolidine-2(S)-ylcarbonyl]thiazole, 2-[1-{3-(4-phenylbutanoyl-2(S)-phenylthiazolin-4(R)-ylcarbonyl}pyrrolidin-2 (S)-ylcarbonyl]thiazole, 2-{1-(1-benzyloxycarbonylpyrrolidin-2(S)-ylcarbonyl)pyrrolidin-2(S)-ylcarbonyl}benzothiazole, 2-{1-(1-benzyloxycarbonylindolin-2(S)-ylcarbonyl)pyrrolidin-2(S)-ylcarbonyl}benzothiazole, 2-[1-{1-(4-phenylbutanoyl)indolin-2(S)-ylcarbonyl}pyrrolidin-2(S)-ylcarbonyl]benzothiazole, 2-{1 -(1-benzyloxycarbonyl-4(R)-phenylthiopyrrolidin-2(S)-ylcarbonyl)pyrrolidin-2 (S)-ylcarbonyl}benzothiazole, 2-[1-{1 -(4-phenylbutanoyl)-4(R)-phenylthiopyrrolidin-2(S)-ylcarbonyl}pyrrolidin-2(S) -ylcarbonyl] benzothiazole, 2-[1-{1-(4-phenylbutanoyl)pyrrolidin-2(S)-ylcarbonyl}pyrrolidin-2(S)-ylcarbonyl]oxazole, 2-[1-{1-(4-phenylbutanoyl)indolin-2(S)-ylcarbonyl}pyrrolidin-2(S)-ylcarbonyl]oxazole, 4,5-dimethyl-2-[1-{1-(4-phenylbutanoyl)pyrrolidin-2(S)-ylcarbonyl}pyrrolidin-2(S) -ylcarbonyl]thiazole, 5-[1-{1-(4-phenylbutanoyl)pyrrolidin-2(S)-ylcarbonyl}pyrrolidin-2(S)-ylcarbonyl]thiazole, 3-[1-{1-(4-phenylbutanoyl)pyrrolidin-2(S)-ylcarbonyl}pyrrolidin-2(S)-ylcarbonyl]1,2,4-triazole, 2-[1-{1-(4-phenylbutanoyl)pyrrolidin-2(S)-ylcarbonyl}pyrrolidin-2(S)-ylcarbonyl]pyrazole, 2-[1-{1-(4-phenylbutanoyl)pyrrolidin-2(S)-ylcarbonyl}pyrrolidin-2(S)-ylcarbonyl]benzoxazole, 2-{1-(1-benzyloxycarbonyl)pyrrolidin-2(S)-ylcarbonyl)pyrrolidin-2(S)-ylcarbonyl}benzimidazole, 2-[1-{1-(4-phenylbutanoyl)pyrrolidin-2(S)-ylcarbonyl}pyrrolidin-2(S)-ylcarbonyl]thiazoline.

4. A pyrrolidin-2-ylcarbonylheterocyclic compound of the formula:

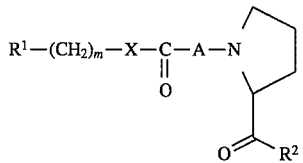

or its salt, wherein:

$R^1$ is aryl;

$R^2$ is a radical selected from the group consisting of 2-thiazole, 2-oxazole, 2-imidazole, 2-pyrrole, 2-thiophene, 2-benzothiazole, 2-benzoxazole, 2-benzimidazole, 4-oxazole, 2-(3,4-dimethylthiazole), 2-indole, 5-thiazole, 2-thiazoline, 2-triazole and 2-pyrazole;

X is O, thiomethylene, or $CH_2$;

A is:

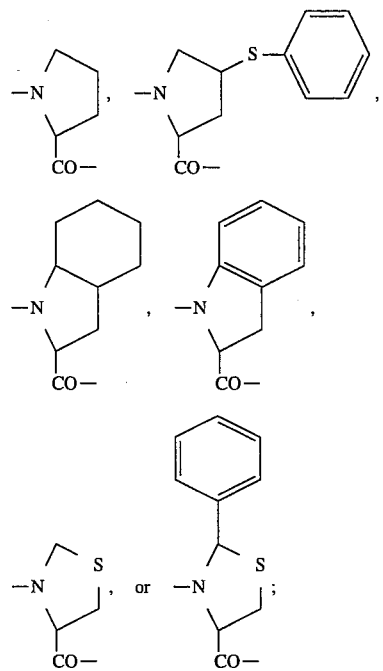

and m is an integer from 1 to 5, and wherein said compound is:

2-[1-(2-benzylthioacetylcyclopentan-1-ylcarbonyl)pyrrolidin-2(S)-ylcarbonyl]thiazole, 2-[1-(2-benzylthioacetylcyclohexan-1-ylcarbonyl)pyrrolidine-2 (S)ylcarbonyl]thiazole, 2-[1-(2-benzylthio-acetylcyclohexan-1-ylcarbonyl)pyrrolidin-2(S)-ylcarbonyl]benzothiazole, 2-{1-(1-benzyloxycarbonylpyrrolidin-2(S)-ylcarbonyl)pyrrolidin-2(S)-ylcarbonyl}thiophene, 2-[1-{1-(4-phenylbutanoyl)pyrrolidin-2(S)-ylcarbonyl}pyrrolidin-2(S)-ylcarbonyl]thiophene, 2-[1 -{1 -(4-phenyl-butanoyl)pyrrolidin-2(S)-ylcarbonyl}pyrrolidin-2(S)-ylcarbonyl]-1 H-imidazole, or 2-[1-{1 -(4-phenylbutanoyl)pyrrolidin-2(S)-ylcarbonyl}pyrrolidin-2(S)-ylcarbonyl]-1 H-benzimidazole.

5. The compound of claim 1, where said $R^2$ radical is joined to the compound by a carbon to carbon bond.

6. The compound of claim 2, where said $R^2$ radical is joined to the compound by a carbon to carbon bond.

7. A composition comprising a compound as claimed in claim 1 and a pharmaceutically acceptable additive.

8. The composition of claim 7, where said $R^2$ radical is joined to the compound by a carbon to carbon bond.

9. A pharmaceutical composition comprising a therapeutically effective amount of the compound as claimed in claim 2 and a pharmaceutically acceptable additive.

10. The composition of claim 9, where said $R^2$ radical is joined to the compound by a carbon to carbon bond.

11. A pharmaceutical composition comprising a therapeutically effective amount of the compound as claimed in claim 3 and a pharmaceutically acceptable additive.

12. A method of inhibiting PEP in a mammalian brain comprising administering a pharmaceutically effective amount of a compound according to claim 1 to a mammalian organism in need of treatment thereof.

13. A method of inhibiting PEP in a mammalian brain comprising administering a pharmaceutically effective amount of a composition according to claim 7 to a mammalian organism in need of treatment thereof.

* * * * *